United States Patent
Huff

(10) Patent No.: US 8,682,417 B2
(45) Date of Patent: Mar. 25, 2014

(54) HEAT-RELATED SYMPTOM DETECTION SYSTEMS AND METHODS

(75) Inventor: Glen Forrest Huff, Riverton, UT (US)

(73) Assignee: Intermountain Invention Management, LLC, Salt Lake City, UT (US)

( * ) Notice: Subject to any disclaimer, the term of this patent is extended or adjusted under 35 U.S.C. 154(b) by 52 days.

(21) Appl. No.: 13/282,451

(22) Filed: Oct. 26, 2011

(65) Prior Publication Data

US 2012/0130251 A1    May 24, 2012

Related U.S. Application Data

(60) Provisional application No. 61/406,915, filed on Oct. 26, 2010.

(51) Int. Cl.
*A61B 6/00* (2006.01)

(52) U.S. Cl.
USPC .... 600/474; 600/473; 600/475; 374/E13.003; 374/121; 374/124; 374/129; 374/137; 702/131

(58) Field of Classification Search
USPC .......... 600/473, 474, 475; 374/E13.003, 121, 374/124, 129, 137; 702/131
See application file for complete search history.

(56) References Cited

U.S. PATENT DOCUMENTS

| | | |
|---|---|---|
| 6,606,115 B1 | 8/2003 | Alicandro et al. |
| 7,340,293 B2 | 3/2008 | McQuilkin |

OTHER PUBLICATIONS

Ng et al. "Analysis of IR thermal imager for mass blind fever screening". Microvascular Research. 68 (2004), pp. 104-109.*
Lim et al. "Human Thermoregulation and Measurement of Body Temperature in Exercise and Clinical Settings". Annals Academy of Medicine, Singapore. (Apr. 2008) vol. 37, No. 4, pp. 347-353.*
Kumar et al. "Correlation Pattern Recognition for Face Recognition". IEEE, Proceedings. (Nov. 2006) vol. 94, No. 11, pp. 1963-1976.*
Thermoteknix Systems Ltd. VisIR 640 FevIR Scan skin temperature measurement system product brochure (as archived Sep. 25, 2009 by WayBack Machine Internet Archive; retrieved Mar. 13, 2013).*
Glazer, *Management of Heatstroke and Heat Exhaustion*, American Family Physician, vol. 71, No. 11, pp. 2133-2140 (Jun. 1, 2005).
Waters, *Heat illness: Tips for recognition and treatment*, Cleveland Clinic Journal of Medicine, vol. 68, No. 8, pp. 685-687 (Aug. 2001).
Garza et al., *Heat-Loss Patterns in National Football League Players as Measured by Infrared Thermography*, InfraMation 2008 Proceedings, 8 pages (May 14, 2008).
Sithinamsuwan et al., *Exertional Heatsroke: Early Recognition and Outcome with Aggressive Combined Cooling—a 12-Year Experience*, Military Medicine, vol. 174, pp. 496-502 (May 2009).
Ortutay, *How thermal-imaging cameras spot flu fevers*, Associated Press, 3 pgs. (May 1, 2009), available at http://www.nbcnews.com/id/30523865/ns/technology_and_science-tech_and_gadgets/t/how-thermal-imaging-cameras-spot-flu-fevers/.
Moran et al., *Core Temperature Measurement*, Current Opinion, Adis International Limited, Sports Med 2002:32 (14), pp. 879-885 (2002).

* cited by examiner

*Primary Examiner* — Long V. Le
*Assistant Examiner* — Colin T Sakamoto
(74) *Attorney, Agent, or Firm* — Stoel Rives LLP

(57) ABSTRACT

Methods for detection of heat-related symptoms can include use of a thermal sensor to obtain thermal data. Subsets of the thermal data can correspond with multiple subjects. The subsets can be compared to determine whether any of the subjects is a thermal outlier relative to the remaining subjects.

26 Claims, 11 Drawing Sheets

HEAT-RELATED SYMPTOM DETECTION SYSTEMS AND METHODS

CROSS-REFERENCE TO RELATED APPLICATIONS

This application claims the benefit under 35 U.S.C. §119 (e) of U.S. Provisional Patent Application No. 61/406,915, titled METHOD AND SYSTEM FOR EARLY THERMOGRAPHIC HEAT ILLNESS RECOGNITION, which was filed on Oct. 26, 2010, the entire contents of which are hereby incorporated by reference herein.

TECHNICAL FIELD

The present disclosure relates generally to systems and methods for detecting heat-related illnesses.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
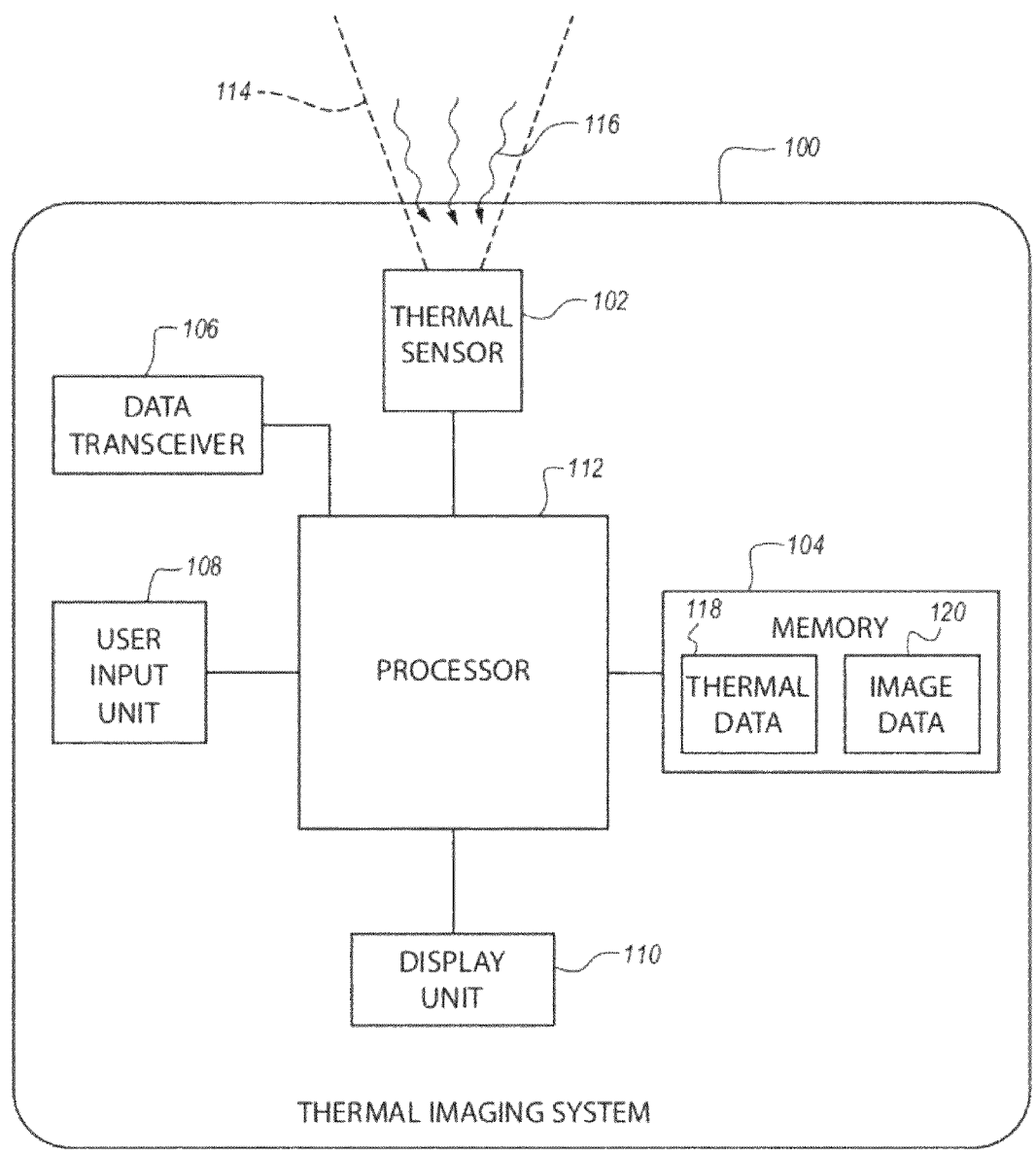
FIG. 1 is a block diagram of an embodiment of a thermal imaging system.

Early detection of symptoms exhibited by an individual that may progress towards a heat-related illness, and/or detection of the onset or early stages of a heat-related illness, can permit avoidance measures to be taken and/or early treatment of the individual, thus averting the illness or lessening its effects. As used herein, the term "individual" refers to any subject for whom medical attention may be desired. The term "individual" may be used herein synonymously with the term "animal subject," and this latter term includes any human or other animal that may benefit from medical or veterinary care in the event of a heat-related illness. The term "individual" can refer to animal subjects who are not under surveillance of trained medical personnel as well as those who are (e.g., non-individuals and individuals).

As used herein, the term "heat-related illness" is a broad term that encompasses illnesses that are typically referred to as "heat illnesses" or "exertional heat illnesses" that can result from elevated temperatures, such as, for example, exertional heat stroke, exertional heat exhaustion, exertional heat cramps, exertional heat injury, dehydration, heat syncope, and/or heat stress. An individual may have one or more medical conditions that increase the risk of developing an exertional heat illness. Accordingly, an exertional heat illness may result from environmental, medical, and/or physiological conditions. Although the disclosure herein can apply to both "heat illness" and "exertional heat illness," the non-limiting examples discussed herein are generally directed to exertional heat illness. Accordingly, term "heat illness" may be used at times, even though the term "exertional heat illness" may be the more appropriate term in the given context. Further, the term "heat-related illness" also encompasses illnesses that result from lowered temperatures, such as, for example, hypothermia. Accordingly, although much of the following discussion focuses on heat illnesses that result from elevated temperatures, applications to other heat-related illnesses will be evident.

By way of example, exertional heat stroke is defined as a severe illness characterized by central nervous system dysfunction, organ and tissue injury with a high core body temperature resulting from strenuous exercise and environmental heat exposure. More generally, individuals who suffer from a heat illness can exhibit signs and symptoms of increased core body temperature (e.g., above about 40° C.), and may suffer from hot, dry skin, dizziness, vertigo, syncope, confusion, delirium, shock, and/or possibly unconsciousness.

Typically, when an individual exercises, the core body temperature of the individual will increase over time and then stabilize at the increased level until exercise is stopped. With heat illness, however, the core body temperature will continue to rise, and this indication can be accompanied or followed by other symptoms of heat illness. Some techniques for monitoring of heat illness consist of identifying at-risk subjects through screening history and physical exam, as well as monitoring signs and symptoms. In other or further techniques, urine concentration with specific gravity can be monitored. In still other or further techniques, an individual's core body temperature can be monitored with ingested temperature probes and/or, where environmental or other conditions are suitable, conventional thermography with highly sensitive and highly accurate equipment. One or more of the foregoing procedures can suffer from shortcomings when used separately or in the combinations just recited. Examples of shortcomings of various procedures, when used separately, are now discussed.

A individual's history may be inaccurate or he may have no prior history to indicate an increased risk of heat illness. Thus, a physical exam will not always identify those at risk for heat illness.

Monitoring for signs and symptoms of heat illness will typically identify individuals when they are developing heat illness, but overlook those who are in the very early stages of an increased body temperature (e.g., an increase in temperature that is greater than normal), and thus are already at an increased risk for heat illness. This can delay treatment to those who are at an increased risk of heat illness.

Urine specific gravity will indicate if the urine is concentrated, which can correlate to dehydration. While dehydration is a risk factor for heat illness, there is not necessarily a one-to-one correlation. Thus, using urine specific gravity can be misleading and lead to inaccurate results.

Ingestible temperature probes generally accurately measure body temperature to allow for evaluation of risk for heat illness. However, the probes can be expensive. In addition, each probe is generally usable over the period of only two to three days. Thus, they can be prohibitively expensive, particularly if they are used with a large number of individuals.

Conventional thermography techniques involve recording temperature measurements from a single subject using highly sensitive and highly accurate instruments. Some studies have shown that temperature measurements are most accurate if taken from a very small area medial to the eyes bilaterally. This poses significant difficulty in obtaining accurate measurements at any distance from the subject. Moreover, highly accurate thermal sensing equipment can be quite expensive. Additionally, the accuracy of measurements of a single subject can be greatly impacted by many variables, such as ambient temperature, wind, sweating, radiation, emissivity, and/or thermal reflection. Such variables can be prevalent in uncontrolled environments, such as an athletic field or venue, a military training field, or a dog or horse racetrack.

In addition, certain thermal cameras that perform thermography can be limited by a relative scale effect, which is commonly used in such cameras. The thermal cameras are generally set up to maximize the contrast in an image by scaling the image on a grayscale, from black to white. The extreme ends of the spectrum typically correspond to the coldest and hottest features within the field of view of the thermal camera. In some instances, the coldest feature corresponds to the black end of the spectrum, whereas in other instances, the coldest feature corresponds to the white end of the spectrum. If a new, hotter feature comes into the field of view of the thermal camera, the feature that was once hottest, and the lightest (or darkest, depending on the settings), will now be identified with a darker (or lighter) color from an intermediate region of the grayscale. This can complicate identification of the exact temperature of the subject, in some instances.

Various embodiments disclosed herein can ameliorate or resolve one or more of the foregoing shortcomings of known techniques. Other and/or further advantages of the embodiments will also be evident from this disclosure.

For example, in some embodiments, relatively inexpensive thermographic equipment can be used due to less reliance, or even no reliance, on determining an accurate temperature of a subject, as the embodiments can instead compare the relative temperatures of multiple subjects. Stated otherwise, some embodiments are designed to detect one or more thermal outliers from a group of subjects, and may further identify the thermal outliers as subjects that are at an increased risk for a heat-related illness. Such a comparative approach among a group of subjects, rather than an absolute approach relative to a single subject, can be desirable in uncontrolled environments, such as an athletic field or venue, military training grounds, a dog or horse racetrack, etc. In some embodiments, it can be desirable for all individuals who are analyzed or monitored to undergo roughly equal amounts of physical exertion so that the identification of thermal outliers more clearly represents a thermal departure from a normal level of the group, as discussed further below.

FIG. 1 is a block diagram of an embodiment of a heat-related illness detection system 100, which may also be referred to as a thermal imaging system 100. In some embodiments, the thermal imaging system 100 comprises a standalone thermographic or thermal imaging camera. For example, in some embodiments, an exterior of the thermal imaging system 100 can appear similar to that of a standard thermal imaging camera, although the internal workings thereof are different. In other embodiments, the thermal imaging system comprises a thermal imaging camera or other temperature sensing device that is coupled with other hardware (e.g., a personal computer or other computing device). In various embodiments, the thermal imaging system 100 can include, for example, a thermal sensor 102, a memory 104, a data transceiver 106, a user input unit 108, a display unit 110, and/or a processor 112. In the illustrated embodiment, the thermal imaging system 100 includes each of these components.

The sensor 102 can be connected to the processor 112. The thermal sensor 102 can comprise, for example, a thermographic sensor that can be configured to detect thermal signals from one or more animal subjects. For example, in some embodiments, the thermal sensor 102 comprises a thermal sensor such as a THERMAL-EYE™ 4500 series imaging camera core, which is available from L-3 Communications Infrared Products of Dallas, Tex. The sensor 102 can have a field of view 114 within which or from which the sensor 102 receives thermal signals 116. In various embodiments, the thermal sensor 102 and/or the processor 112 is configured to convert the thermal signals 116 into thermal data 118, or temperature data, or stated otherwise, can be configured to generate thermal or temperature data 118 from the thermal signals 116. In some embodiments, the thermal sensor 102 comprises a two-dimensional array of pixels, where each pixel is configured to gather information regarding properties of the thermal signal received within the area defined by the pixel. For example, the sensor 102 can be configured to determine for each pixel the temperature associated with the thermal signal 116 received thereat, and the thermal data 118 can include information regarding the position of the pixel and the temperature observed thereat.

The memory 104 can be connected to the processor 112 and/or any other suitable component of the system 100. The memory 104 can store the temperature data 118, and similarly, the temperature data 118 can be retrieved from the memory 104. In some embodiments, the processor 112 can be configured to generate image data 120, or information for forming an image of the field of view 114 that is observed by the thermal sensor 102. For example, the processor 112 can be configured to assign one or more of a shade from a grayscale, a shade (or color) from a color spectrum or color bar (discussed below), a pattern, or a symbol to each pixel of the thermal data 118 to thereby prepare image data 120 from the thermal data 118. The image data 120 can be stored in the memory 104. Generation of an image from the image data 120 is discussed further below. It is noted that in many embodiments, at least a portion of the thermal data 118 may be subsumed within the image data 120. For example, the thermal data 118 may include pixel information that is preserved when the image data 120 is formed from it. It may also be said that the image data 120 includes the thermal data 118, since the image data 120 can be derived from the thermal data 118. Accordingly, in some instances, performing an operation on the image data 120 may also be referred to as performing the operation on the thermal data 118.

The data transceiver 106 can be connected, for example, to the processor 112. The data transceiver 106 can be used to communicate data between the thermal imaging system 100 and an external system. For example, in some embodiments, the data transceiver 106 can be used to communicate data from the thermal imaging system 100 to a printer, a storage device, and/or some other peripheral system, and/or the transceiver 106 can be used to communicate data to the thermal imaging system 100 from the one or more peripheral systems.

The user input unit 108 can be connected to the processor 112. The user input unit 108 can be used to interface with a user and thus can comprise, for example, one or more buttons, keyboards, scroll balls, mouse controllers, touch screens, and/or any other suitable device for interfacing with a user.

The user input unit 108 can be used to receive instructions and/or other user input data into the system 100. The input data can be used, for example, to provide instructions, adjust settings, and/or indicate a desired operation of the thermal imaging system 100.

The display unit 110 can be connected to the processor 112 such that the processor 112 can deliver the image data 120 to the display unit 110. The display unit 110 can be configured to provide an image 130 (see FIG. 2) of the field of view 114 based on the image data 120.

In various embodiments, the system 100 can be used to identify thermal outliers from a group of individuals (e.g., animal subjects) that are observed via the thermal sensor 102. As used herein, the term "thermal outlier" is used in an ordinary sense, and can refer to an individual that demonstrates thermal characteristics that are anomalous, statistically distinct, or otherwise distinguishable relative to other individuals within a group. For example, in some embodiments in which statistical algorithms are used (as discussed below), a thermal outlier may be defined as having thermal data that deviates from the thermal data of the remaining members of a group by no less than a given number of standard deviations (e.g., 0.5, 0.75, 1, 1.5, 2, 2.5). In many instances, it can be desirable for all individuals within a group to undergo similar amounts of physical exertion prior to observation such that a meaningful normalized, baseline, or average temperature can be determined for the group as a whole (or for a portion of the group).

In some embodiments, the system 100 is dependent on user interaction therewith in order for thermal outliers to be identified. In other embodiments, the system 100 can be fully automated, such that the system 100 autonomously performs a procedure for identifying a thermal outlier.

Figure 2:
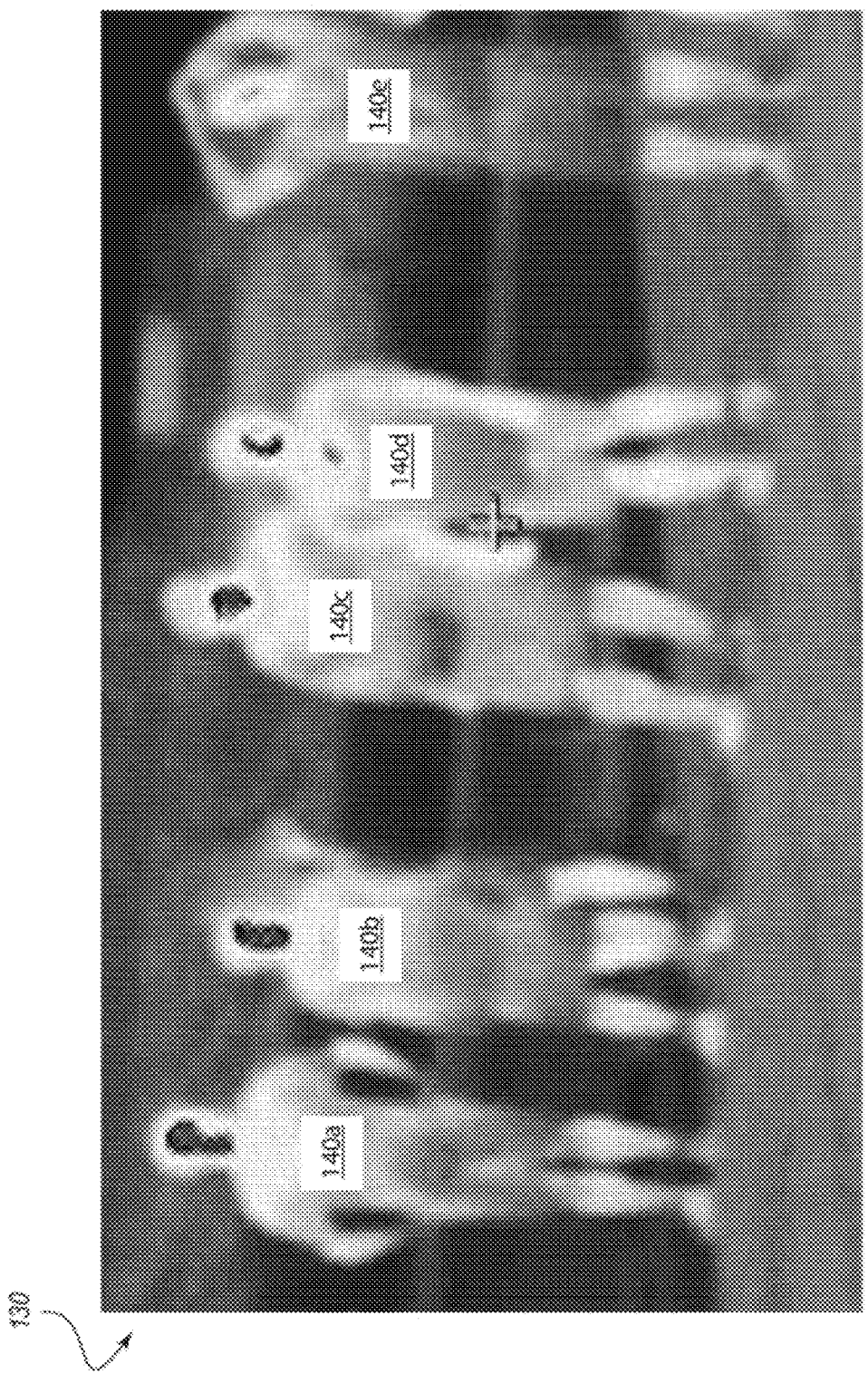
FIG. 2 is an image created using an embodiment of a thermal imaging system such as that depicted in FIG. 1.

With reference to FIG. 2, in certain embodiments, the display unit 110 can provide an image 130, as generated from the image data 120, which includes some portions that are in gray scale and other portions that are highlighted, colorized, or otherwise distinguished from the gray scale portions (e.g., by symbols, patterns, and/or other visual devices). For example, the image data 120 can be associated with a color when the temperature data 118 indicates that the temperature of the associated sensor 102 pixel is at a certain temperature. A portion of the image data 120 can be associated with a first color (e.g., yellow) where the associated thermal data 118 correspond to a first temperature (or temperature range). Portions of the image data 120 associated with a second temperature (or temperature range), which may be adjacent to and higher than the first temperature (or temperature range), may be provided with a second color (e.g., blue). Since the second color corresponds to a higher temperature than does the first color, the second color may be referred to herein as a "higher color" than the first color. In other or further embodiments, portions of the image data 120 that are associated with a third temperature (or are within a third temperature range) that is adjacent to and higher than the second temperature (or temperature range) may have a third color (e.g., red). Since the third color corresponds to a higher temperature than the second color, the third color may be referred to herein is a "higher color" than each of the first and second colors. Any suitable number of colors may be used for a color scale or color bar such as just discussed (examples of such color bars are identified by reference numerals 150*a*, 150*b*, 150*c* in FIGS. 4-6, which include colors 151*a*, 151*b*, 151*c*; 152*a*, 152*b*, 152*c*; and 153*a*, 153*b*, 153*c*, respectively). In some embodiments, only a single color is used, which may indicate when a subject is at risk for a heat-related illness. However, in other embodiments (such as described below), multiple colors (e.g., 2 or more or 3 or more) may be used, with only the "highest" color indicating that a subject may be at risk for a heat-related illness. Such a multi-color arrangement of the color bar can facilitate or provide meaningful "base lining" of color bar, as discussed further below.

FIG. 2 includes five subjects 140*a*, 140*b*, 140*c*, 140*d*, 140*e* that have each run the same distance over approximately the same period of time. Stated otherwise, the five subjects 140*a*, 140*b*, 140*c*, 140*d*, 140*e* have undergone approximately the same amount of physical exertion at the time of observation. The clothed regions of the subjects 140*a*, 140*b*, 140*c*, 140*d*, 140*e* are cooler than the unclothed regions, from the perspective of the thermal sensor 102. Accordingly, the clothed regions of the subjects are shown in grayscale. Environment surrounding the runners is also shown in grayscale. However, a color bar such as described above, has been adjusted such that a lower end of the lowest color (yellow) corresponds with the lowest temperature of the facial regions of the subjects. In the black-and-white image of FIG. 2, this yellow coloration of the facial regions appears white. The legs of the runners also includes yellow coloration, as these portions of the subjects are at a temperature that falls within the lowest color range. Central regions of the subjects' faces are colored blue (which appears substantially black in the black-and-white image of FIG. 2). However, no portion of any of the subjects is colored red. Accordingly, in this embodiment, none of the five subjects 140*a*, 140*b*, 140*c*, 140*d*, 140*e* is identified via the colors of the color bar as a thermal outlier relative to the remaining subjects, and thus none of the subjects appears to have a heightened risk for a heat-related illness.

In certain embodiments, each of the first, second, and third colors can be associated with a separate range of temperatures, which ranges can be adjacent to each other. For example, each temperature range can span a fixed temperature increment. In some embodiments, the temperature increment can be, for example, 1° C. In another embodiment, the lowest temperature associated with the color bar and/or the temperature increments of the color bar can be adjusted by the user using the user input unit 108. For example, the lowest color (yellow) can span a 1° C. temperature increment that ranges from 37.5° C. to 38.5° C., the middle color (blue) can span a 1° C. temperature increment that ranges from 38.5° C. to 39.5° C., and the highest color (red) can span a 1° C. temperature increment that ranges from 39.5° C. to 40.5° C. Other ranges and increments are also possible. For example, in some embodiments, the different colors may span temperature ranges that are not equally incremented.

Figure 3:
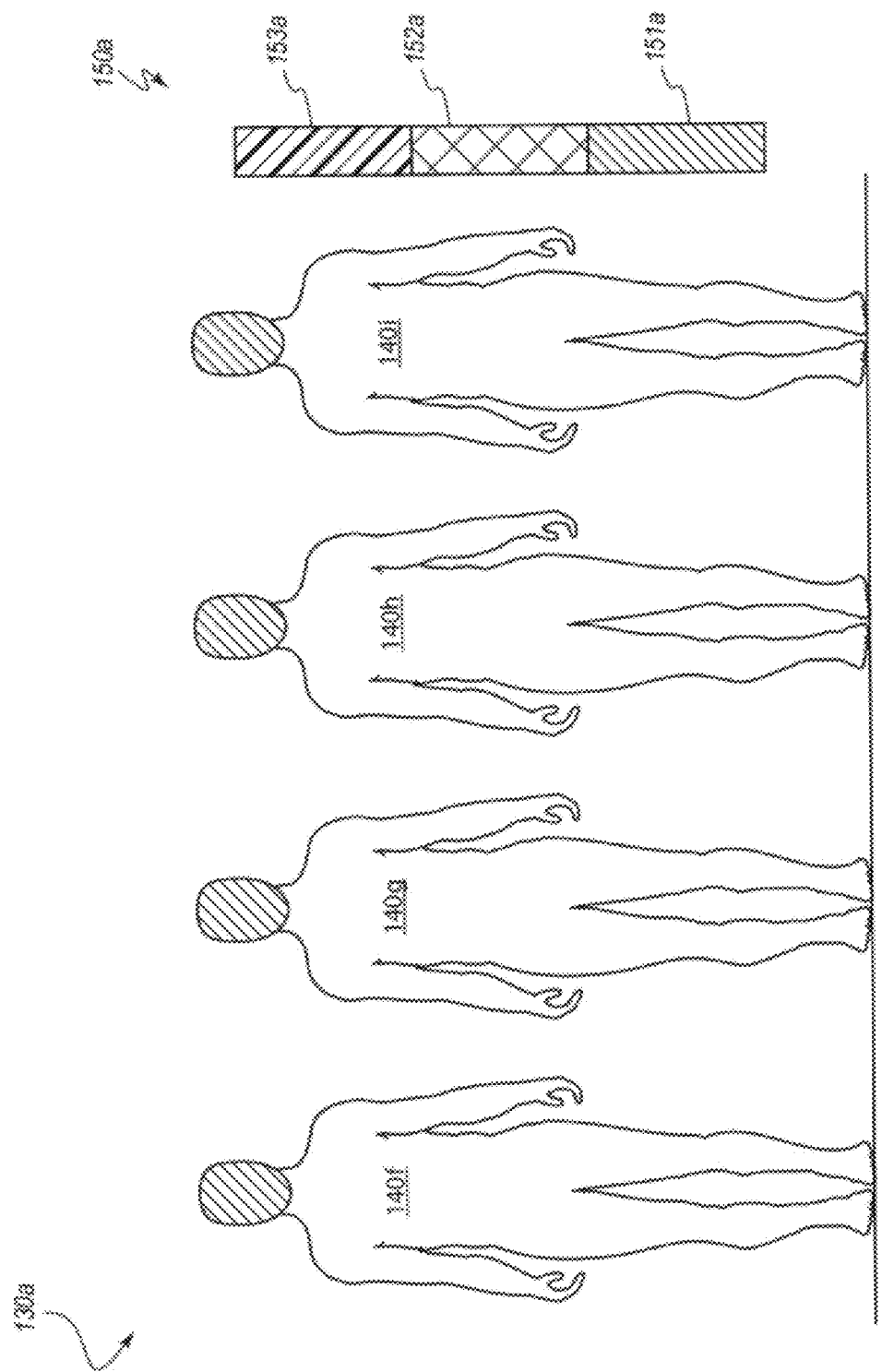
FIGS. 3-5 are schematic views of multiple images of a group of subjects, wherein the images were created using an embodiment of a thermal imaging system such as that depicted in FIG. 1.
Figure 4:
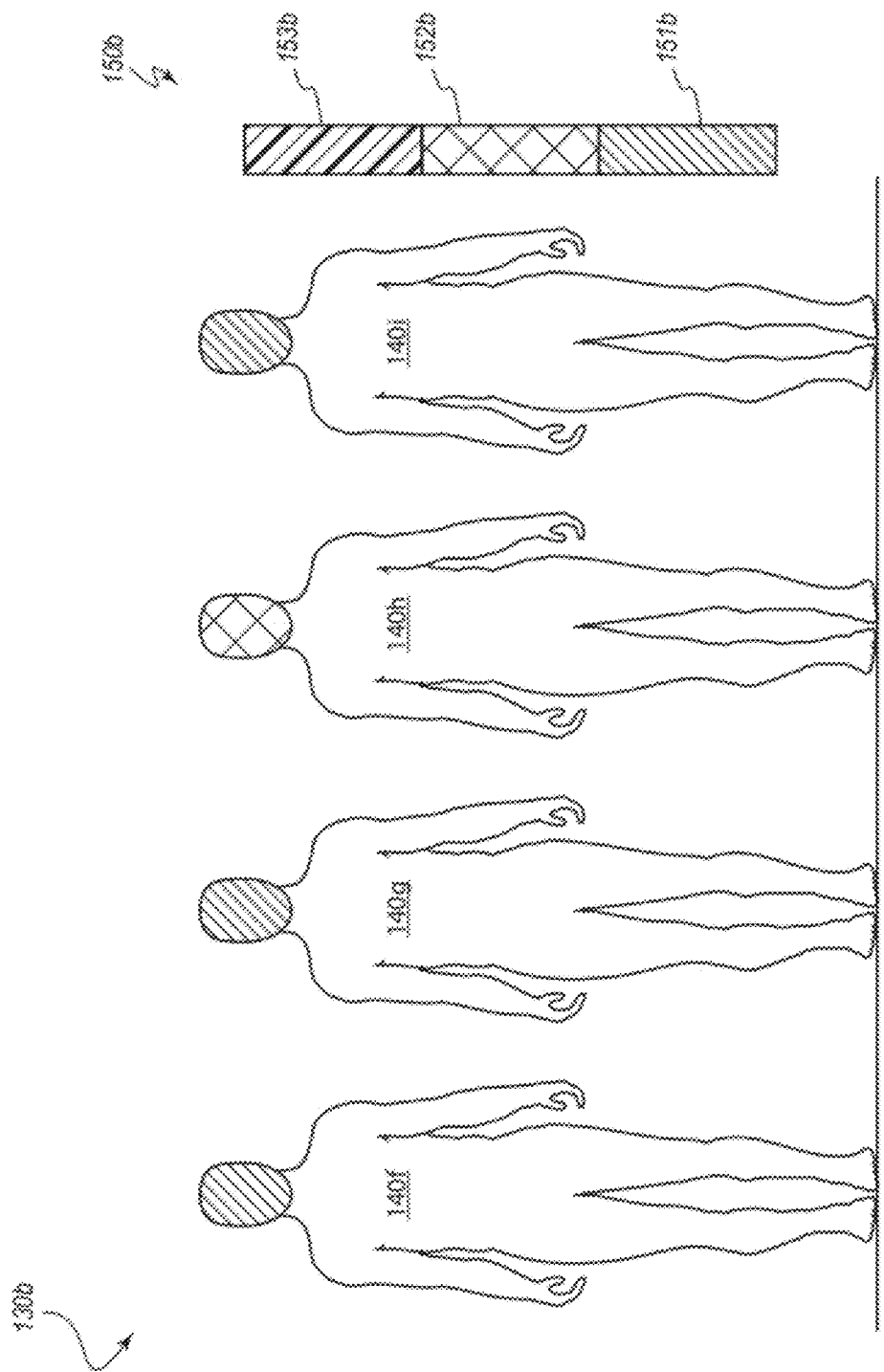
Figure 5:
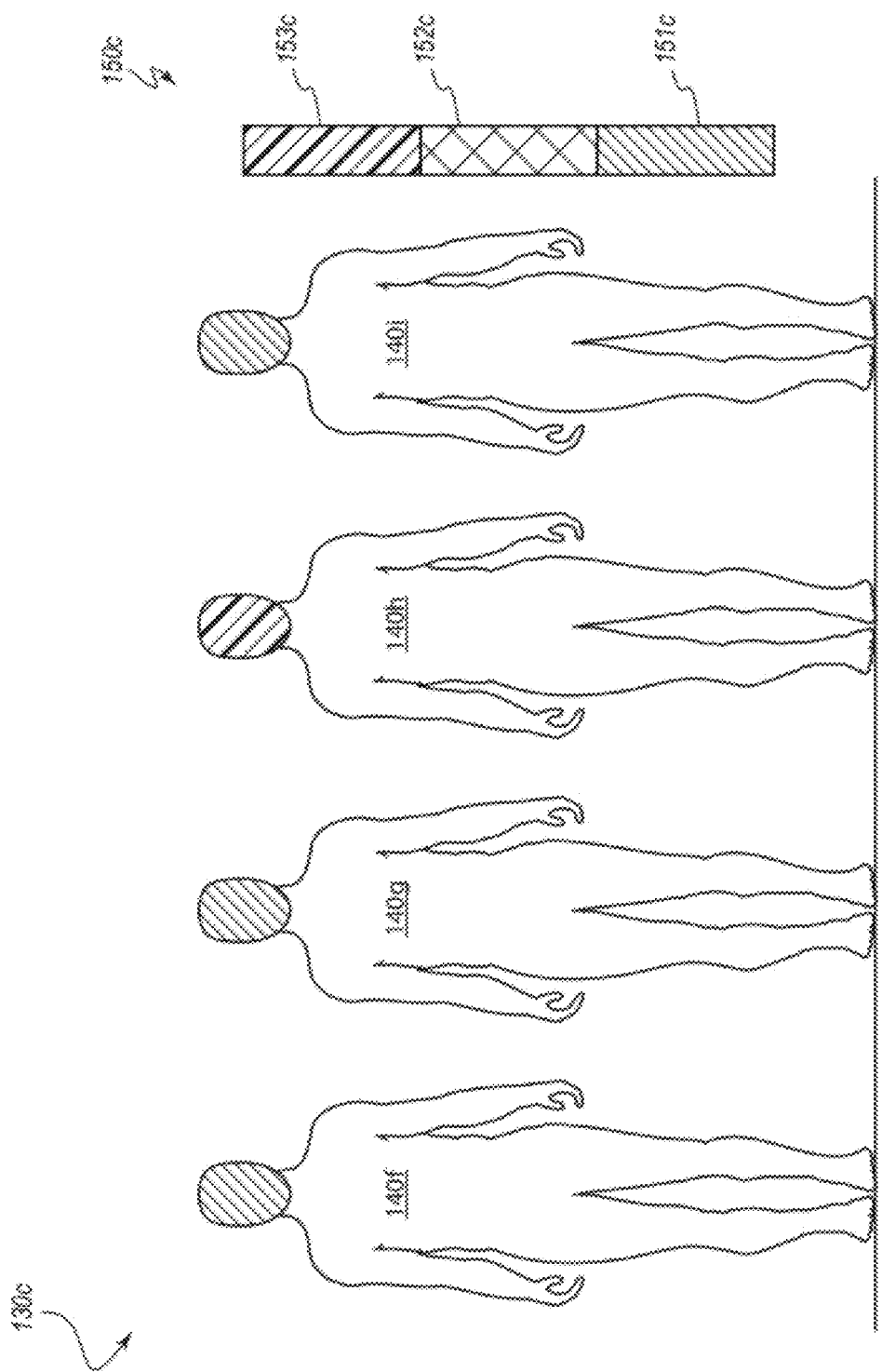

FIGS. 3-5 schematically depict thermal images 130*a*, 130*b*, 130*c* obtained via an embodiment of a thermal imaging system such as the system 100 described above, and FIG. 6 depicts a plot 160 of core temperature data continuously obtained over the period that the thermal imaging system gathers data for the images 130*a*, 130*b*, 130*c*. In the illustrated trial, thermal data is collected for four runners 140*f*, 140*g*, 140*h*, 140*i* at the completion of each of 12 laps around a race track. The images 130*a*, 130*b*, 130*c* are associated with the completion of laps 5, 8, and 11, respectively. In particular, at the completion of each lap, a thermal image of the runners is obtained via the thermal sensor 102, and the thermal image is stored as thermal data.

Figure 6:
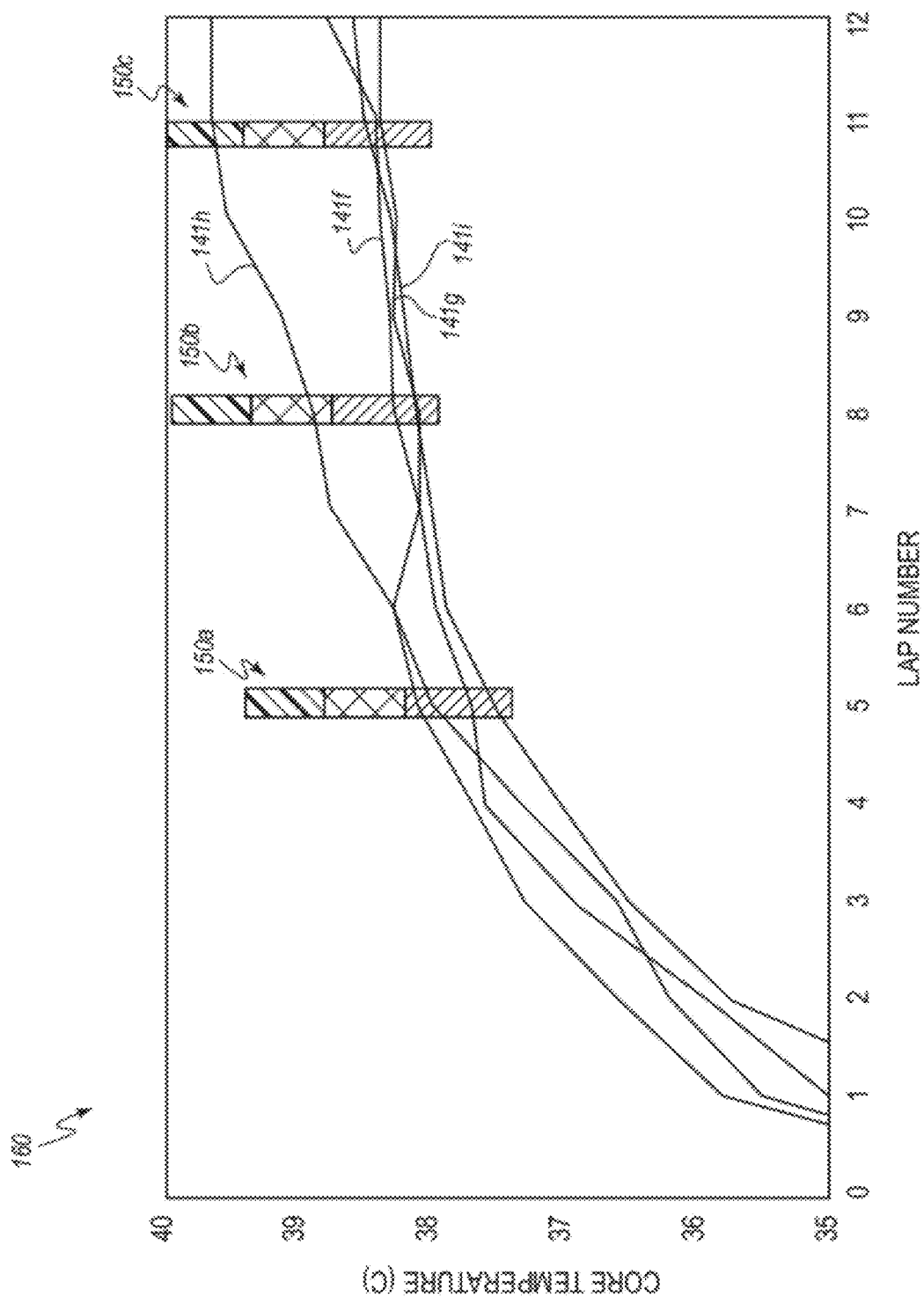
FIG. 6 is a plot of the core temperatures of the subjects, wherein the plot is correlated with the images of FIGS. 3-5.

With reference to FIG. 3, the color bar 150*a* includes low, mid, and high colors 151*a*, 152*a*, 153*a*. For the thermal data corresponding with the completion of the fifth lap, the color bar is adjusted along a thermal scale until the low end of the low color 151*a* corresponds with an extreme temperature (in this case, the lowest temperature) of all of the faces of the runners 140*f*, 140*g*, 140*h*, 140*i*. As can be seen in FIG. 6, the low end of the color bar 150a at this stage is at about 37.3° C. As shown in FIG. 3, the temperatures of each runner's face are entirely within the low color range.

With reference to FIG. 4, the color bar 150b is identical to the color bar 150a (and includes low, mid, and high colors 151b, 152b, 153b), except that it has been adjusted upwardly to account for the fact that the body temperature of each runner has increased due to the additional physical exertion during laps 6, 7, and 8. Once again, for the thermal data corresponding with the completion of the eighth lap, the color bar 150b is adjusted along a thermal scale until the low end of the low color 151b corresponds with the lowest temperature of all of the faces of the runners 140f, 140g, 140h, 140i. As can be seen in FIG. 6, the low end of the color bar 150b at this stage is at about 37.9° C. As shown in FIG. 4, the facial temperatures of each of the runners 140f, 140g, and 140i are entirely within the low color range. However, at least a portion of the face of the runner 140h is within the mid color range of temperatures.

In some embodiments, it may be determined that a subject is a thermal outlier and thus is at a heightened risk of heat-related illness when at least a portion of the subject is within the mid color range while the other subjects are exclusively in the low color range, or when a predominant portion of the subject is within the mid color range while the other subjects are predominantly within the low color range. However, in other embodiments, it may be determined that a heightened risk of heat-related illness exists when at least a portion of the subject is within the high color range while the other subjects are exclusively in the low and/or mid color ranges. Any such suitable method for identifying when an animal subject is a thermal outlier and is at a heightened risk of a heat-related illness is contemplated.

With reference to FIG. 5, the color bar 150c is identical to the color bar 150b (and includes low, mid, and high colors 151c, 152c, 153c), except that it has been adjusted upwardly to account for the fact that the body temperature of each runner has increased slightly due to the additional physical exertion during laps 9, 10, and 11. Once again, for the thermal data corresponding with the completion of the eleventh lap, the color bar 150c is adjusted along a thermal scale until the low end of the low color 151c corresponds with the lowest temperature of all of the faces of the runners 140f, 140g, 140h, 140i. As can be seen in FIG. 6, the low end of the color bar 150c at this stage is at about 40.0° C. As shown in FIG. 5, the facial temperatures of each of the runners 140f, 140g, and 140i remain entirely within the low color range. However, at least a portion of the face of the runner 140h is within the high color range of temperatures Based on the different colors in the facial regions of the runners 140f, 140g, 140h, 140i, in some embodiments, it may be concluded that the runner 140h is a thermal outlier relative to the outer runners 140f, 140g, 140i, and thus may be at a heightened risk for a heat-related illness. Providing contrasting coloring schemes to the facial or other physiological regions of a subject may be considered as an identification of the thermal outlier.

Note that although entire facial potions are colored with a single color in FIGS. 3-5, in many instances, only a portion of each face will exhibit one or more of the colors of the color bars 150a, 150b, 150c. The solid coloring is provided in these illustrative drawings for the sake of simplicity. For example, in some embodiments, a thermal outlier can be identified if any portion of the face (or any other suitable portion of the subject) corresponds with the highest color.

The process of upwardly adjusting a color bar so as to correspond with the lowest temperature of a physiological region of test subjects can be referred to as normalization of the color bar or as base lining of the color bar. The base lining process may be considered to be a form of comparison of subsets of thermal data. In particular, the subsets of thermal data that are associated with the faces of the runners are compared, as the color bar is adjusted relative to the faces and thermal outliers are identified based on color deviations.

As can be appreciated from the foregoing, the grayscale portions of the images 130a, 130b, 130c may change from one to another, such as may result from temperature fluctuations in the environment surrounding the runners (e.g., if extremely hot or cold objects enter the field of view 114 of the thermal sensor 102). However, such fluctuations of the grayscale portions will not affect the identification of thermal outliers, since, in some embodiments, the gradations of the color bar 150 are fixed from one image 130 to the next, and the baseline of the color bar is adjusted relative to the subjects (or a portion thereof), and not the environment.

In some embodiments, the temperature ranges of the various colors 151, 152, 153 of a given color bar 150 can be adjusted by the user using the user input unit 108. For example, a user may wish to encompass more or fewer portions of the image data in the first color 151, the second color 152, and/or the third color 153. In other embodiments, such adjustments may be automated via the processor 112 (e.g., according to a statistical algorithm or other set of predefined rules). The display unit 110 can also display a color bar 150 to serve as a guide for the colors in the image data and can indicate the relationship between the first color, the second color, and/or the third color in a sequential manner so that users can determine which colors are the higher colors. In some embodiments, the color bar 150 can be manually adjusted by the user using the user input unit 108 so as to correlate the lower end of the color bar 150 to the coolest region of the faces of the runners.

In other or further embodiments, the processor 112 can automatically adjust the color bar 150. For example, in some embodiments, the processor 112 may adjust the color bar relative to one or more subjects based on statistical algorithms, predefined rules, and/or a user's preferences, which may be entered into the system 100 via the user input unit 108. The processor 112 can also adjust color values and/or shades of the color bar 150 depending on the user's preferences through the user input data from the user input unit 108. The adjusted image data can be displayed on the display unit 110.

In FIGS. 3-6, only a "snapshot" of thermal signals was obtained at the completion of each lap. Moreover, the system 100 was substantially fixed in a single physical orientation. In other embodiments, the system 100 can be configured to operate continuously (e.g., more as a video camera than as a still camera) and/or may be readily movable so as to keep a group of subjects within the field of view 114 of the sensor 102.

With reference again to FIG. 6, the core temperature data is obtained via ingestible temperature probes and is monitored substantially continuously. The temperature probes provide accurate temperature readings over time, that are traced as the temperature progression curves 141f, 141g, 141h, 141i, which correspond with the runners 140f, 140g, 140h, 140i, respectively. Any suitable statistical analysis of the temperature progression curves 141f, 141g, 141h, 141i can be used to determine that at some point during the upper laps, the runner 140h becomes a thermal outlier relative to the other runners 140f, 140g, 140i. Depending on how the outlier conditions are defined, this point may be somewhere around any of laps 7 through 12. The plot 160 confirms that the system 100 can accurately identify thermal outliers.

Figure 7:
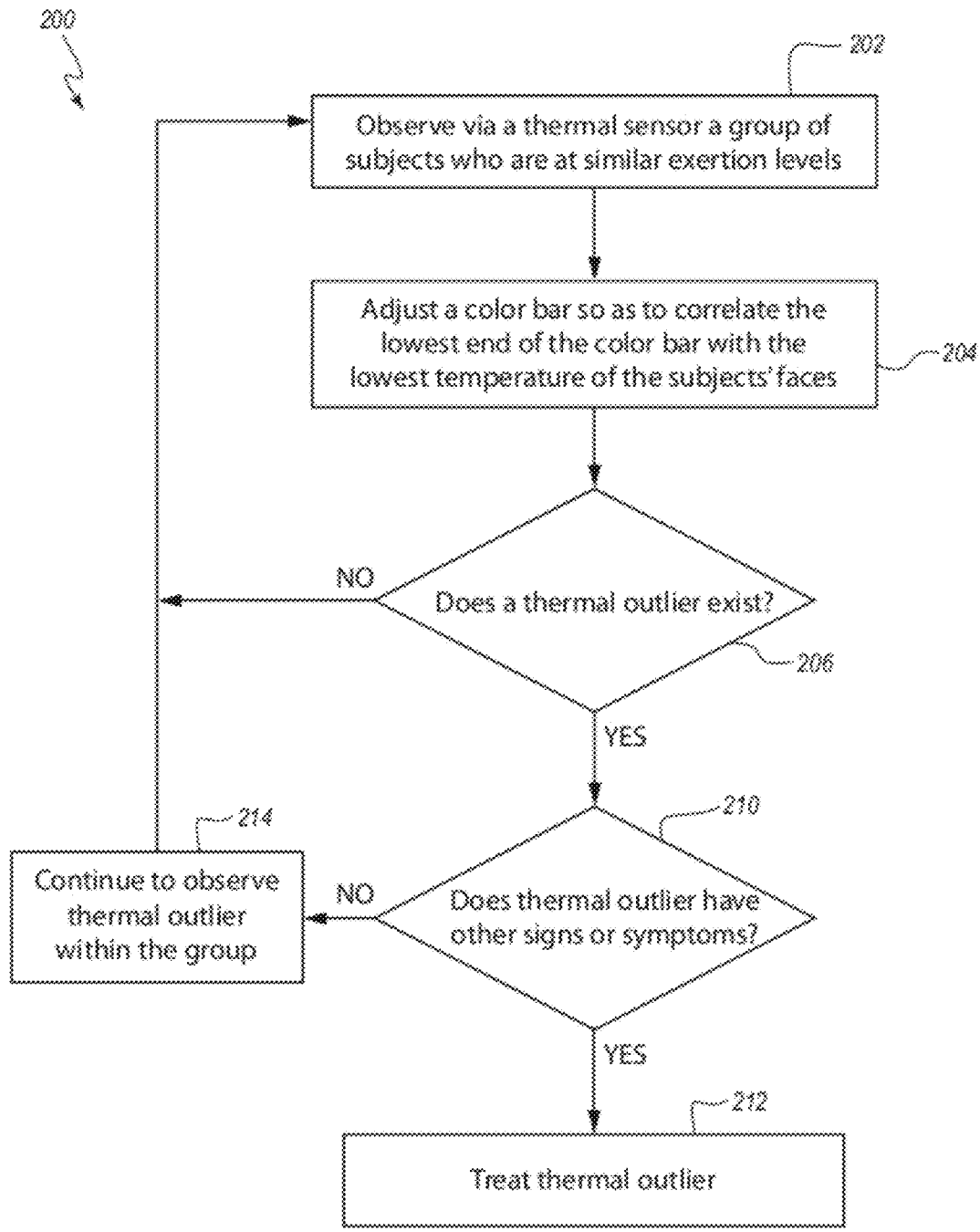
FIG. 7 is a flow diagram of an illustrative method for identifying a thermal outlier from a group of subjects using an embodiment of a thermal imaging system.

FIG. 7 depicts an illustrative method 200 for identifying a thermal outlier that can be employed with a system, such as the thermal imaging system 100 discussed above. At block 202, a group of subjects who are at similar levels of physical exertion are observed via a thermal imaging system. For example, a group of athletes can be selected as subjects and the thermal imaging system 100 can be positioned such that the sensor 102 can capture thermal and image data from the athletes. The athletes can be, for example, athletes in similar situations, such as athletes that have performed approximately the same amount of exercise for the same amount of time.

In some embodiments, it can be desirable for a large number of subjects to be observed via the sensor 102, as this can aid in more readily identifying thermal outliers, in certain embodiments. For example, a larger sample size N can yield more meaningful or accurate statistical results. A large number of subjects used for the sake of comparison can also reduce a likelihood that all of the athletes will have abnormally elevated temperatures and/or be suffering from heat illnesses. In various embodiments, the number of observed subjects is no fewer than 3, 4, 5, 6, 7, 8, 9, or 10. However, it is understood that groups of small or larger number of athletes can be selected for comparison.

At block 204, a color bar is adjusted so that the lowest end of the bar correlates with the lowest temperature of the athletes' faces. For example, in some embodiments, this can be achieved using the user input unit 108, as previously discussed. The user can adjust the temperature associated with lowest color in the color bar so that the athletes' faces displayed in the display unit 110 have a color corresponding to the lowest color on the color bar. In other embodiments, this can be achieved automatically via the processor 112. In still other embodiments, a color bar is not used (as discussed below). Rather, the various temperatures of the athletes are directly compared to each other.

At decision block 206, a determination is made as to whether any athletes have a higher temperature, as indicated by a higher color than the other athletes. For example, in some embodiments, a user can visually inspect the display unit 110 to determine whether any of the athletes have a higher temperature, which can be demonstrated by a higher color (e.g., blue or red) than that found in the images of the other athletes (e.g., yellow). In other embodiments, the processor 112 can determine whether any of the athletes have a higher temperature, as indicated by a higher color than the other athletes. In other embodiments in which a color bar is not used, the temperature measurements can be directly compared to each other in any suitable manner. For example, statistical operations may be performed to determine whether one or more temperatures observed with respect to one of the subjects statistically deviates from the temperatures observed with respect to the remaining subjects.

If none of the athletes has an outlying higher temperature (e.g., as indicated by a higher color than the other athletes), the process repeats itself, beginning again at block 202. This can indicate that none of the athletes have been detected as being at risk for heat illness.

Otherwise, if an athlete is detected with an outlying temperature, as indicated by a higher color than the other athletes, then the method proceeds to decision block 210. At this block, the athlete is evaluated to determine if there are other signs or symptoms to indicate heat illness. If there are no other signs or symptoms to indicate heat illness, then the method proceeds to block 214. The outlier athlete can continue to be observed with other athletes and the process can repeat, beginning at block 202. It may be desirable to pay special attention to the outlier athlete after having passed through block 210 in this manner, as the outlier athlete may soon develop other signs or symptoms. For example, in some embodiments, it may be desirable to monitor the athlete via other methods, such as reviewing the athlete's medical history, conducting a urine specific gravity check, administering an ingestible temperature probe, and/or taking a temperature reading via a highly sensitive thermographic camera.

If the athlete does have other signs or symptoms that indicate heat illness at block 210, then the athlete is treated at block 212, and the athlete can also be further evaluated by coaches, trainers, and/or doctors. Such treatment can include, for example, cooling the athlete, rehydrating the athlete, and/or any other types of treatment suitable for someone suffering from heat illness.

In some embodiments, the processor 112 can provide a warning with respect to a thermal outlier that is detected at block 206. For example, the processor 112 can provide a message via the display unit 110 that the athlete should be further evaluated. Such a message could include highlighting the athlete in some manner or providing text or other indicators on, near, or associated with the athlete. In still other or further embodiments, the processor 112 can cause an alarm to sound.

As can be appreciated from the foregoing, in certain embodiments, a system can determine whether or not an individual has the initial or more advanced stages of a heat illness based on a comparative analysis of subjects who are in similar environments and/or at similar exertion levels. The individual can be identified as a thermal outlier who may have initial or more advanced stages of heat illness when his temperature increases anomalously relative to the other subjects' temperatures. This approach can be beneficial, in certain instances, as the absolute and exact temperature of any single athlete is unimportant, which can eliminate the dependency on the accuracy of the sensor 102 to determine a precise temperature of a subject. Thus, heat illness can be detected with cheaper equipment, in more diverse situations, and with more accurate results.

Although the use of color is described to represent the temperature for certain image data 120, other representations can be used in addition to or instead of colors. For example, in some instances, numbers or other characters can be used. In other or further embodiments, symbols may be used. For example, "+" and "−" symbols can be used; in some instances, a "+" symbol can indicate an increased temperature relative to an average temperature, while a "−" symbol can indicate a decreased temperature relative to the average temperature, or only a slightly increased temperature relative to the average temperature. In some embodiments, multiple pixels are used to create a single symbol. In other or further embodiments, shapes or shadings may also be used. Although a few examples of representations are disclosed, it is understood that other representations may also be used which can provide information regarding the relative temperature of the subjects.

In some embodiments, the processor 112 or another processor can compute a thermal risk value based on the image data of each athlete. The thermal risk value can be the result of statistical calculations, such as a weighting of the number of data in the image data which corresponds to each color. For example, a single pixel of a first color can have a first weight, a single pixel of a second color can have a second weight, and a single pixel of a third color can have a third weight. This can allow, for example, a more accurate reflection of the true increase in temperature of each athlete, and thus provide a more accurate assessment of the heat illness risk for each athlete. Each weighted pixel value may be normalized to account for the total number of pixels present for each subject. For example, some subjects may be closer to the sensor 102 and thus have more pixel data, as compared with other subjects who are further from the sensor 102.

In other embodiments, systems can be used to identify a thermal outlier without first assigning color information to the thermal data. For example, rather than weighting pixel colors, an algorithm can weight the temperatures of the relevant pixels of the thermal data. The processor 112 may thereafter identify a subject that is in the image data as a thermal outlier. For example, the processor 112 may store with the image data color information or other information to highlight or otherwise identify the thermal outlier. In other embodiments, the processor 112 may instead leave the image data pixels unaltered, but may instead overlay the pixels with a warning message after generation of the image via the display unit 110.

Figure 8:
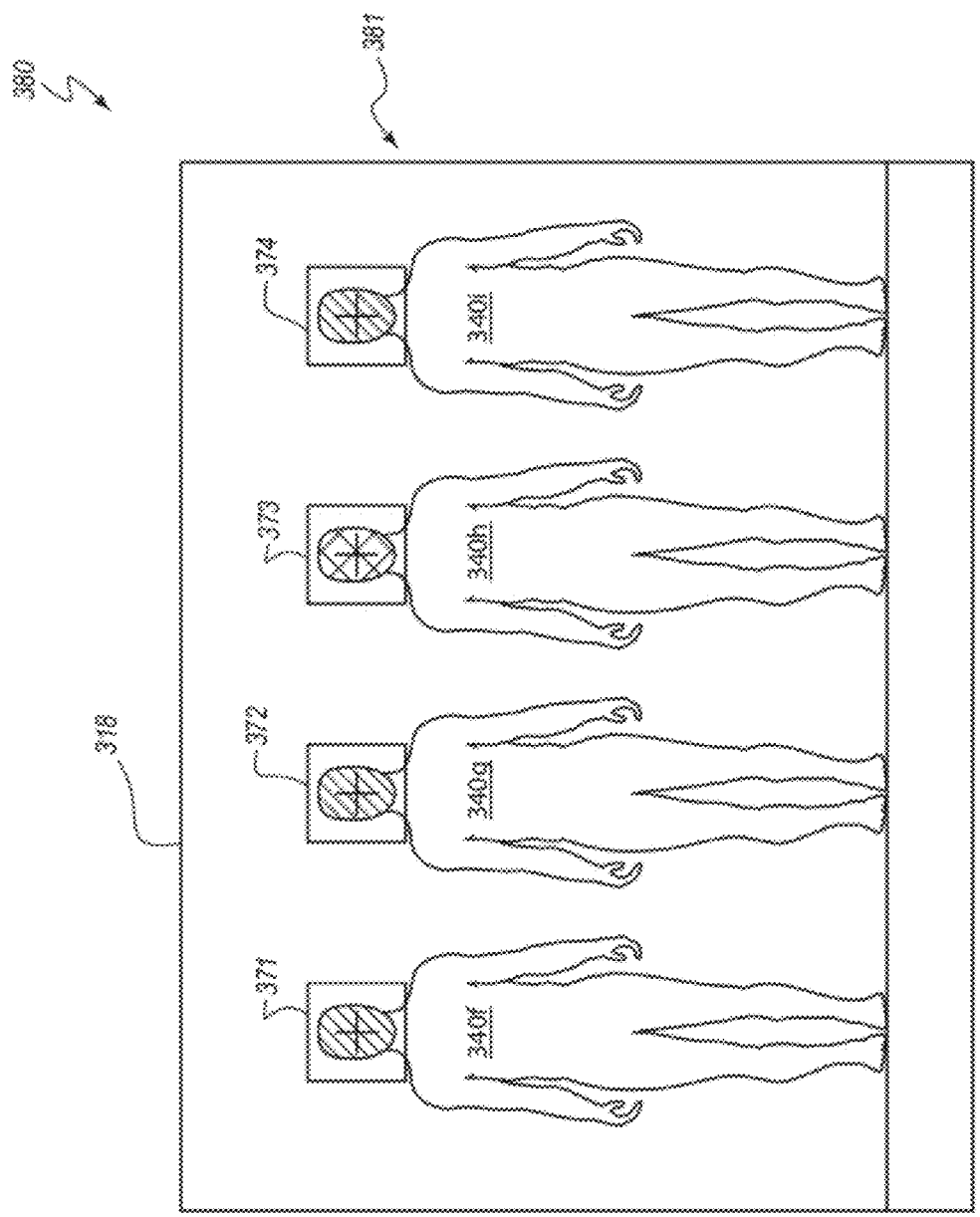
FIG. 8 is a schematic view of thermal data obtained from group of subjects that depicts an early stage of another illustrative method for identifying a thermal outlier from a group of subjects.
Figure 9:
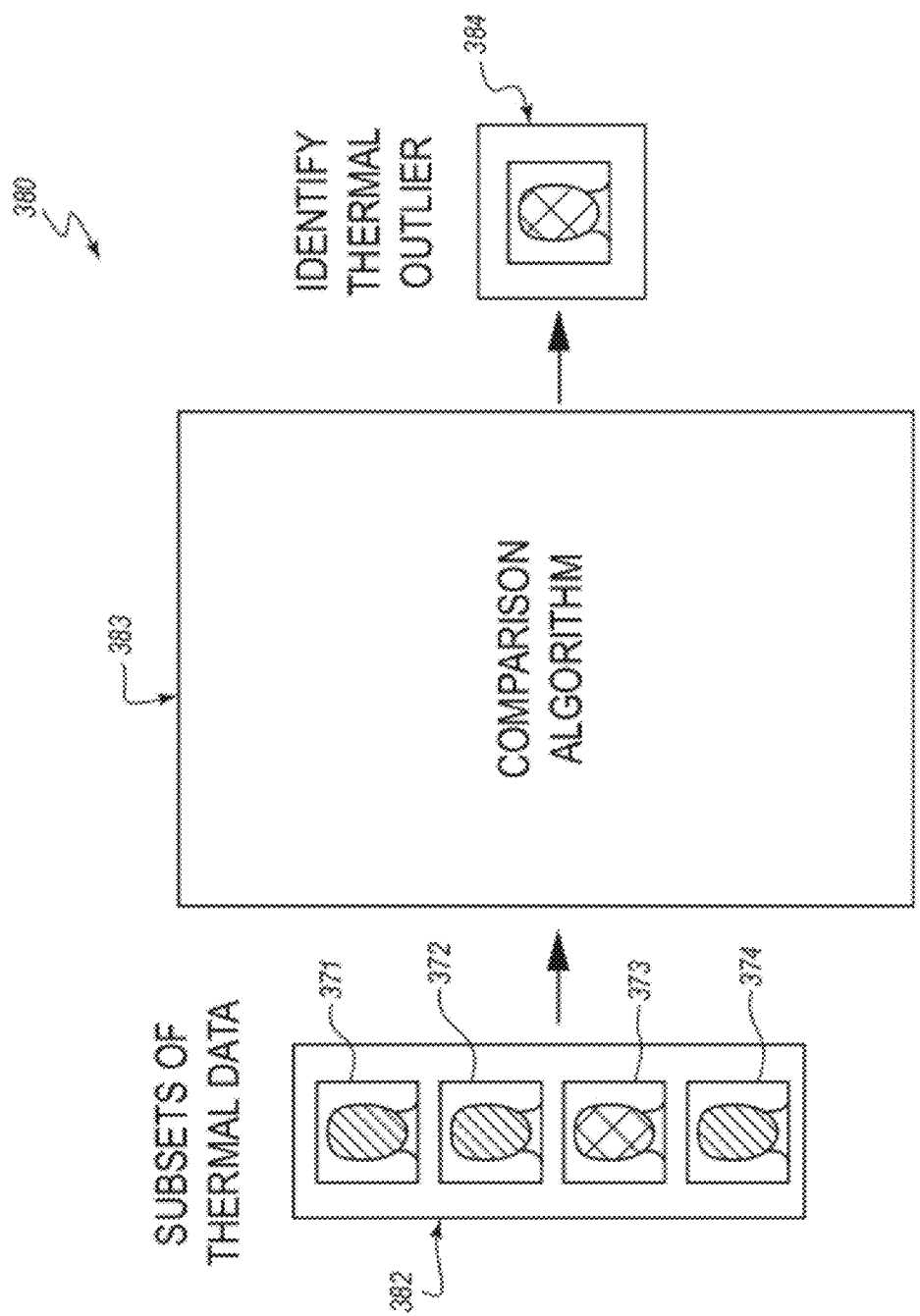
FIG. 9 is a flow diagram of additional stages of the illustrative method of FIG. 8.

FIGS. 8 and 9 depict stages of another illustrative method 380 that is used to identify a thermal outlier from a group of individuals. The method 380 can be carried out, whether in whole (e.g., in a fully automated manner) or in part (e.g., in an at least partially manual manner) via a thermal imaging system such as the system 100 described above with respect to FIG. 1.

In an early stage 381 of the method 380, the thermal sensor 102 can receive thermal signals 114 from a group of individuals 340f, 340g, 340h, 340i that are simultaneously within the field of view 114 of the sensor 102, as shown in the depiction of stage 381 in FIG. 8. As discussed further below, in other embodiments, one or more of the individuals 340f, 340g, 340h, 340i may not be within the field of view 114 simultaneously with the remaining individuals. One or more of the sensor 102 and the processor 112 can generate thermal data 318 from the thermal signals 114. In FIG. 8, the thermal data 318 is depicted in a pictorial format, wherein the picture is comprised of many pixels. The thermal data 318 may instead be stored in a matrix or other suitable storage configuration that identifies each pixel and its representative thermal information.

With reference to FIGS. 8 and 9, at another stage of the method 380, a separate subset 371, 372, 373, 374 of the thermal data that corresponds with at least a portion of each animal subject 340f, 340g, 340h, 340i, respectively, can be identified. In the illustrated embodiment, this identification comprises one or more of identification of pixels that are associated with a physiological feature of the subjects 340f, 340g, 340h, 340i and isolation of the pixels, along with their associated thermal information in separate data storage structures. The identification can be carried out by the processor 112. For example, in some embodiments, the processor 112 may be configured to identify faces within a thermal image, and can be configured to isolate the pixels associated with the faces. In other methods, such as described above, the process of identifying may instead take place with respect to the image data (which can be said to include the thermal data) after an image has been formed via the display unit. Certain of such methods can be at least partially manual, as a user may visualize the faces or other physiological portions of the subjects in order to adjust a color bar, such as described above.

With reference to FIG. 9, the method 380 can further include a stage 383 in which the subsets of thermal data are compared to determine whether any of the subjects 340f, 340g, 340h, 340i is a thermal outlier relative to the remaining subjects. Any suitable comparison algorithm may be used. For example, as discussed above, the comparison algorithm may employ any suitable statistical method or methods in order to identify a deviation in temperature for one of the subjects. Such an algorithm may be programmed into the processor 112. In other or further embodiments, the comparison may include a determination of whether or not a given subject has a "highest color" (e.g., red). Such a comparison may be made via the processor 112 and or via a user (manually), as discussed above.

The method 380 can further include a stage 384 in which a subject is identified as a thermal outlier. In some embodiments, the identification information is stored within the image data (e.g., color bar information), such that the stage 384 may occur prior to generation of an image (such as the image 130 in FIG. 2) of the field of view 114 of the thermal sensor 102. In other embodiments, the image may be generated, and then an identifying tag or other suitable graphic, or some other identification mechanism (e.g., an audible sound) can be associated with the thermal outlier.

In certain instances, the comparison algorithm 383 may not result in identification of a thermal outlier. In such instances, other stages of the method 380 can be repeated until a thermal outlier is identified. Accordingly, the method 380 can monitor the subjects 340f, 340g, 340h, 340i over time. In some implementations of the method 380, a thermal image is produced via the display unit 110 at each iteration so that a user of the system 100 can monitor the progress of the method 380.

In some embodiments, the memory 104 can store multiple sets of thermal data 118 and/or image data 120. For example, the memory 104 may store one set for each iteration. In further embodiments, the comparison algorithm 383 may use multiple sets of the thermal data 118 and/or image data 120 to determine whether any of the temperature of any of the subjects 340f, 340g, 340h, 340i statistically deviates from that of the other subjects over time.

In still further embodiments, the subsets of thermal data 371, 372, 373, 374 can be correlated with a specific subject 340f, 340g, 340h, 340i for one or more iterations. For example, in some embodiments, the processor 112 may use facial recognition software to identify each stet of thermal data, for each iteration, with a unique subject 340f, 340g, 340h, 340i. Such correlation may be useful in determining statistical deviation over a period of time. Such correlation may also be useful where all of the subjects 340f, 340g, 340h, 340i are not simultaneously within the field of view 114 of the sensor 102.

In some embodiments, the method 380 can include setting a threshold value at which a heightened risk for a heat-related illness exists. In certain embodiments discussed above, such setting of a threshold value can comprise altering the color bar, which inherently sets a lower limit of the "highest color" (e.g., red). In other embodiments, a statistical algorithm may be used to determine a deviation factor (e.g., some number of standard deviations) beyond which it is determined that a subject is at risk of a heat-related illness. If the threshold is bypassed, those portions of the subject that exceed the threshold value can be assigned a risk identifier. The term "risk identifier" is used herein to signify any suitable identification by which a risk can be determined. For example, in certain embodiments discussed above, assigning a risk identifier can comprise associating the highest color (e.g., red) with certain pixels. Other risk identifiers can comprise symbols, portions of symbols, patterns, numbers, characters, etc., as discussed above. In some embodiments a "caution identifier" may be used. The caution identifier can correspond to a mid-temperature color (e.g., blue), which may not be sufficient to indicate that a subject is thermal outlier, but which may nevertheless indicate that a subject has more extreme temperatures than other subjects (see, e.g., FIG. 4 and FIG. 6 at lap 8).

Figure 10:
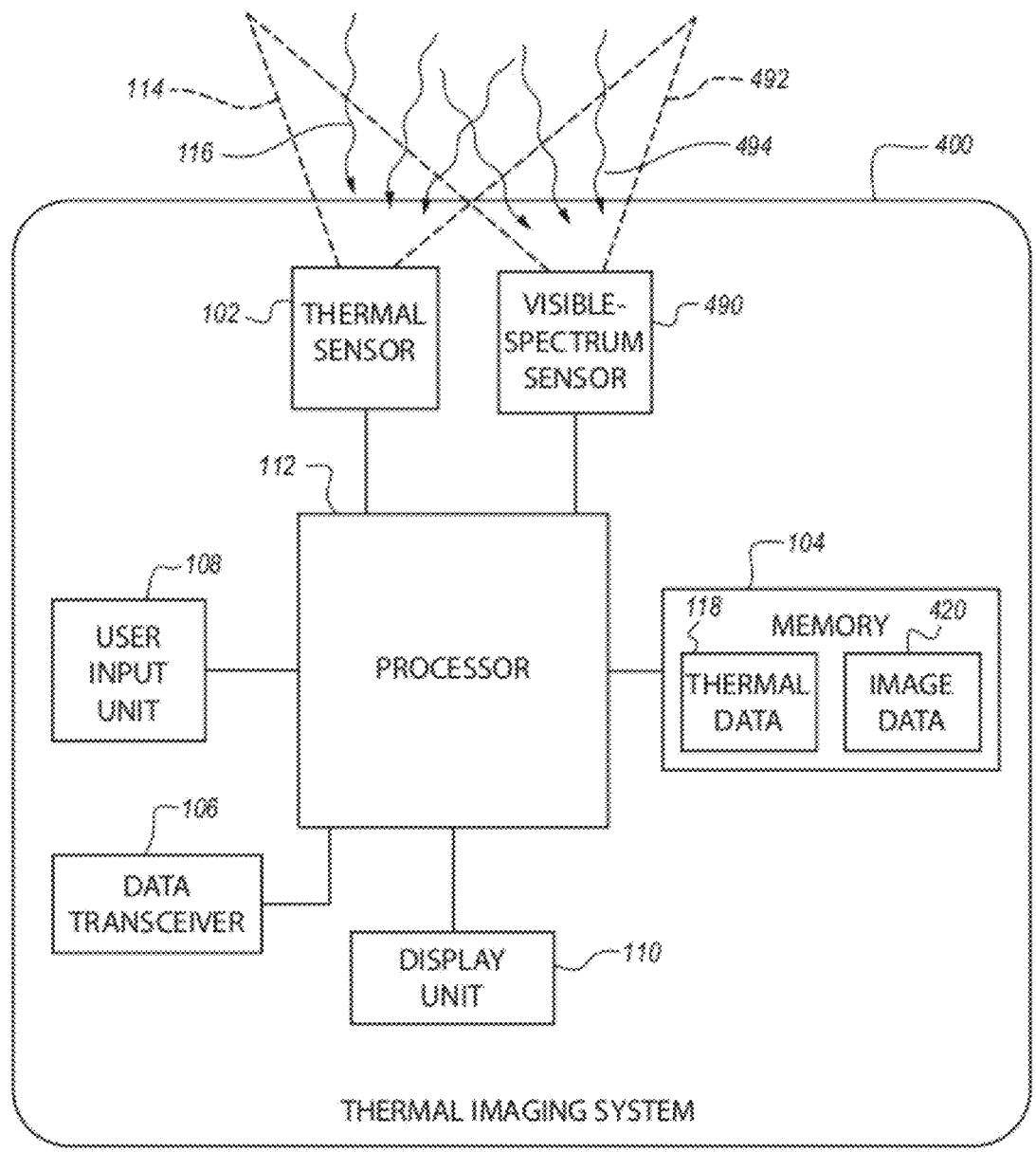
FIG. 10 is a block diagram of another embodiment of a thermal imaging system that includes a visible-spectrum sensor.

FIG. 10 depicts another embodiment of a thermal detection system 400, which can resemble the system 100 discussed above in many respects. Accordingly, like elements are identified with like reference numerals. In addition to the thermal sensor 102, the system 400 includes a visible-spectrum sensor 490 that is coupled with the processor 112. The visible-spectrum sensor 490 has a field of view 492. In the illustrated embodiment, the fields of view 114, 492 of the thermal sensor 102 and the visible-spectrum sensor 490 are substantially overlapping or coextensive. Accordingly, similar images can be produces via the information obtained by the sensors 102, 490. The visible-spectrum sensor 490 is configured to receive or detect visible-spectrum signals 494 (e.g., visible light). The visible-spectrum sensor 490 can comprise any suitable camera.

Figure 11:
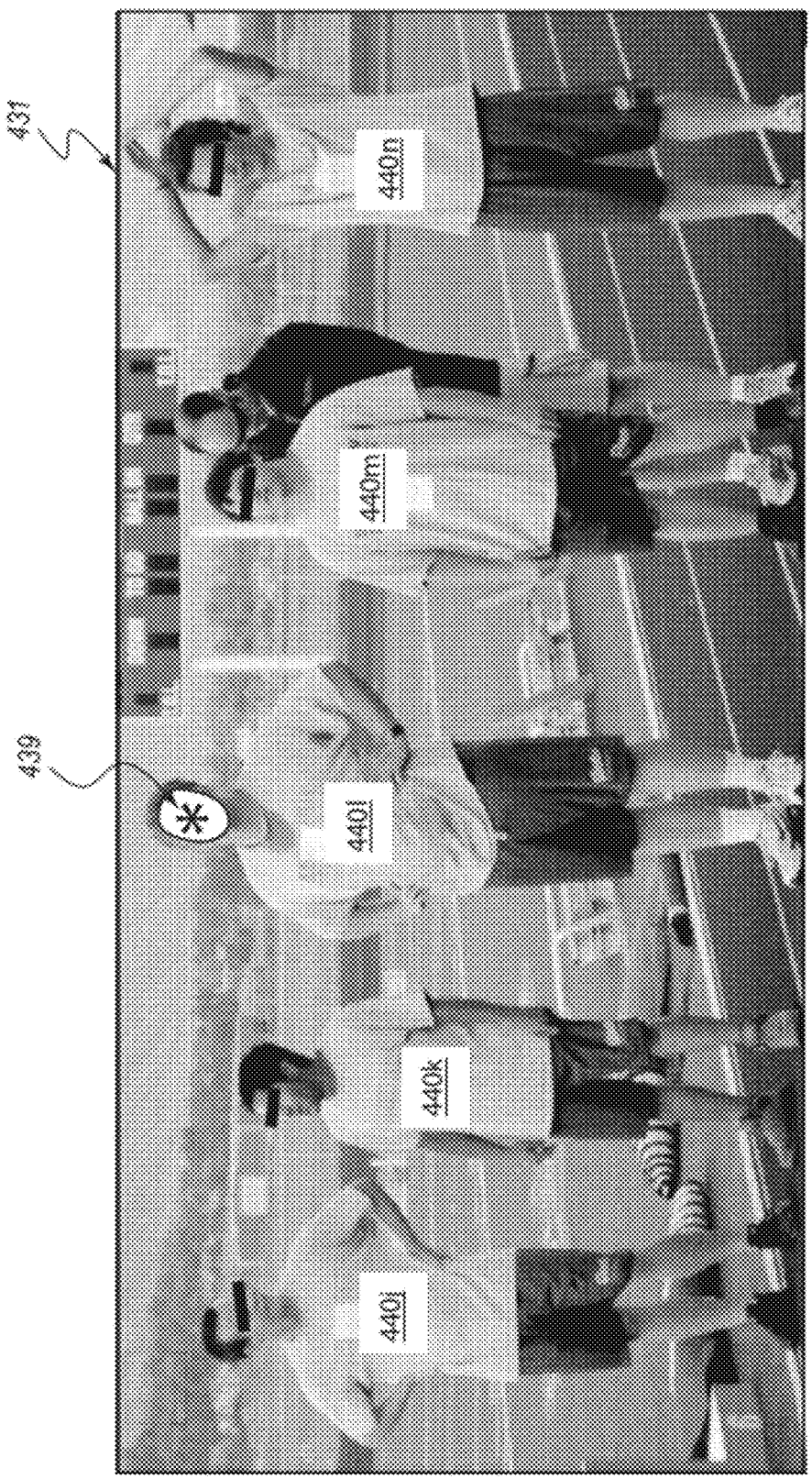
FIG. 11 is an image produced via the system of FIG. 10 in which a thermal outlier is identified.

The visible-spectrum sensor 490 is configured to deliver visible-spectrum image data 420 to the processor 112, which may store the data 420 in the memory 104. In some embodiments, the processor 112 is configured to communicate with the display unit 110 such that the display unit provides a visible-spectrum image 430, as shown in FIG. 11. The processor 112 can utilize the thermal data 118 to determine whether any of the subjects 440$j$, 440$k$, 440$l$, 440$m$, 440$n$ is a thermal outlier. This determination can be made in any suitable manner, such as those discussed above. The processor 112 can further correlate the outlier information with the image data 420 and can coordinate for a risk identifier 439 to be displayed with or over, or to otherwise be associated with, a thermal outlier 440$l$. In some embodiments, the processor 112 uses facial recognition software to correlate the thermal data 118 and the image data 420. Any suitable method discussed above can be performed via the system 400 in manners such as described above with respect to the system 100.

As can be appreciated from the foregoing disclosure, in some embodiments, a thermal imaging system can be used to detect temperature data of a subject and to generate a gray scale image with colorization of portions of the image based on the temperature data. This can allow a group (e.g., of athletes) to be imaged together or roughly concurrently and to comparatively determine if one or more of the individuals in the group have an exertional heat illness. When individuals are imaged together (or closely together in time) in a similar environment, while competing at a similar level, then the individual with a heat illness will stand out with a different color that indicates a higher temperature. This reduces a dependence on the accuracy of the sensor of the thermal imaging system.

Certain embodiments provide for recognition of an increased risk for heat illness early in the disease process so that therapy can be started sooner. Certain embodiments can permit monitoring of larger groups of subjects and identify the at risk subject in the crowd. Monitoring performed by some embodiments can be done done in real time to allow for quick and accurate results, which can be beneficial in situations where time is of the essence such as for athletic or military applications.

In some embodiments, a method for determining heat illness in a group of individuals including detecting temperature data for a group of individuals, generating image data for a first individual in the group of individuals and a second individual in the group of individuals using the temperature data, and comparing a color of the image data corresponding to the first individual in the group of individuals and a color of the image data corresponding to the second individual in the group of individuals to determine whether the first individual in the group of individuals or the second individual in the group of individuals has a heat illness.

In other embodiments, a thermal imaging system for determining heat illness in a group of individuals includes a sensor for detecting temperature data for a group of individuals, a processor connected to the sensor and configured to generate image data for a first individual in the group of individuals and a second individual in the group of individuals using the temperature data, and compare a color of the image data corresponding to the first individual in the group of individuals and a color of the image data corresponding to the second individual in the group of individuals to determine whether the first individual in the group of individuals or the second individual in the group of individuals has a heat illness.

As previously mentioned, in some embodiments, sensors and associated methods discussed herein can be used in identifying thermal outliers that are at risk for heat-related illnesses other than heat illness. For example, some embodiments can be used to identify a thermal outlier who is at risk of hypothermia. For example, with reference again to FIGS. 3-6, an operator of the system 100, or the processor 112, could correlate the upper end of the color bars 150$a$, 150$b$, 150$c$ with the maximum temperatures of the faces of the subjects 140$f$, 140$g$, 140$h$, 140$i$. A thermal outlier would be identified as the individual whose minimum temperature is significantly lower than that of the remaining individuals.

In some embodiments and methods, the systems 100, 400 can be used to identify thermal outliers other than animal subjects. For example, the systems 100, 400 may instead be used to identify thermal anomalies in industrial applications, such as, for example, monitoring manufacturing processes and/or monitoring the temperatures of electronic devices.

Various embodiments, or portions thereof, are described herein in terms of various functional components and processing steps. A skilled artisan will appreciate that such components and steps may be implemented as any number of hardware or software components or combination thereof configured to perform the specified functions. For example, an illustrative embodiment may employ various graphical user interfaces, software components, and database functionality.

For the sake of brevity, conventional techniques for computing, data entry, data storage, and/or the like may not be described in detail herein. Furthermore, the connecting lines shown in various figures contained herein are intended to represent illustrative functional relationships and/or communicative, logical, and/or physical couplings between various elements. A skilled artisan will appreciate, however, that many alternative or additional functional relationships or physical connections may be present in a practical implementation of the systems or methods.

As will be appreciated by those of ordinary skill in the art, principles of the present disclosure may be reflected in a computer program product on a computer-readable storage medium having computer-readable program code means embodied in the storage medium. Any suitable tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture including implementing means which implement the function specified. The computer program instructions may also be loaded onto a computer or other programmable data processing apparatus to cause a series of operational steps to be performed on the computer or other programmable apparatus to produce a computer-implemented process, such that the instructions which execute on the computer or other programmable apparatus provide steps for implementing the functions specified.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Moreover, any suitable combination of features among the various embodiments is contemplated. For example, some systems are described as being capable of continuous operation. Such continuous operation may also be possible with other embodiments.

The claims following this written disclosure are hereby expressly incorporated into the present written disclosure, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶6. Embodiments of the invention in which an exclusive property or privilege is claimed are defined as follows.

The invention claimed is:

1. A method comprising:
receiving, via a thermal sensor that has a field of view, thermal signals from a group that comprises no fewer than three animal subjects, wherein the animal subjects of the group are simultaneously present within the field of view of the thermal sensor while the thermal signals are received;
generating a set of thermal data only from the thermal signals received from the group of simultaneously present animal subjects;
identifying, for each animal subject, a subset of the thermal data that corresponds with at least a portion of the animal subject;
determining a baseline for the group of animal subjects from the subsets of thermal data;
comparing the subsets of thermal data to the baseline to determine whether the subset of thermal data for any of the animal subjects statistically deviates from the baseline such that the animal subject associated with the statistically deviant thermal data is a thermal outlier relative to the remaining animal subjects;
generating an image of the field of view of the thermal sensor; and
identifying an animal subject within the image that corresponds to the thermal outlier.

2. The method of claim 1, wherein identifying a subset of the thermal data comprises identifying a subset of the thermal data that corresponds with a physiological portion of the animal subject.

3. The method of claim 2, wherein the physiological portion includes a portion of the face of the animal subject.

4. The method of claim 1, wherein said comparing the subsets of thermal data comprises statistically analyzing the subsets of thermal data.

5. The method of claim 1, wherein each animal subject within the group has undergone similar amounts of physical exertion.

6. The method of claim 1, further comprising performing multiple iterations of said receiving thermal signals, generating thermal data, identifying subsets of thermal data, determining a baseline, comparing the subsets of thermal data, and generating an image so as to monitor the animal subjects over time.

7. The method of claim 6, further comprising determining whether the thermal data for a given animal subject statistically deviates from the thermal data for the remaining animal subjects over time.

8. The method of claim 6, further comprising correlating multiple subsets of thermal data with a specific animal subject.

9. The method of claim 8, wherein said correlating comprises performing facial recognition on the thermal data that corresponds with the animal subjects.

10. The method of claim 1, further comprising providing a warning if any of the animal subjects is a thermal outlier relative to the remaining animal subjects.

11. The method of claim 10, wherein the warning comprises one or more of sounding an alarm and displaying a message on a screen.

12. The method of claim 1, wherein the heat-related illness is an exertional heat illness.

13. The method of claim 1, further comprising setting a threshold value at which a heightened risk for a heat-related illness exists.

14. The method of claim 13, wherein said setting of a threshold value is based on a comparison of the subsets of thermal data to each other, and wherein said identifying within the image an animal subject as a thermal outlier comprises identifying those portions of the animal subject that exceed the threshold value.

15. The method of claim 14, wherein the portions of the animal subject that exceed the threshold value are assigned a risk identifier.

16. The method of claim 15, wherein the risk identifier comprises one or more of a color and a symbol.

17. The method of claim 14, wherein the portions of the animal subject that exceed the threshold value are assigned a first color, and wherein other portions of the animal subject that are below the threshold value are assigned a second color that is different from the first color.

18. The method of claim 17, further comprising:
receiving thermal signals over a period of time;
generating multiple sets of thermal data from the thermal signals;
identifying, for each set of thermal data and for each animal subject, a subset of the thermal data that corresponds with at least a portion of the animal subject; and
generating multiple images of the field of view,
wherein said comparing the subsets of thermal data comprises:
identifying an extreme temperature from among all of the subsets of the thermal data that correspond with at least a portion of each animal subject for a given set of thermal data, and
setting the one or more temperatures with which the risk identifier is associated relative to the extreme temperature, and
wherein determining whether any of the animal subjects is a thermal outlier relative to the remaining animal subjects comprises determining whether any of the subsets of thermal data that correspond with the animal subjects contains one or more pixels that have been assigned the risk identifier.

19. The method of claim 18, wherein the extreme temperature is a minimum temperature.

20. The method of claim 18, wherein said identifying an extreme temperature from among all of the subsets of the thermal data that correspond with at least a portion of each animal subject takes place for multiple sets of thermal data, and wherein the one or more temperatures with which the risk identifier is associated changes over time.

21. The method of claim 17, wherein each pixel is assigned one of the risk identifier, a caution identifier, and a shade from the graduated scale of shades, wherein the caution identifier corresponds with one or more temperatures that are adjacent to the one or more temperatures associated with the risk identifier.

22. A method comprising:
receiving, via a thermal sensor that has a field of view, thermal signals from a group that comprises physiological portions from no fewer than three animal subjects that are simultaneously present within the field of view of the thermal sensor while the thermal signals are received;
generating a set of thermal data only from the thermal signals received from the group of simultaneously present physiological portions;
identifying a subset of the thermal data that corresponds with each physiological portion;
determining a baseline for the group of physiological portions from the subsets of thermal data;
comparing the subsets of thermal data to the baseline to determine whether the subset of thermal data for any of the physiological portions statistically deviates from the baseline such that the physiological portion associated with the statistically deviant thermal data is a thermal outlier relative to the remaining physiological portions;
generating an image of the field of view of the thermal sensor; and
identifying a physiological portion within the image that corresponds to the thermal outlier.

23. The method of claim 22, wherein each physiological portion comprises a portion of a separate face.

24. The method of claim 22, further comprising performing multiple iteration of said receiving thermal signals, generating thermal data, identifying subsets of thermal data, determining a baseline, comparing the subsets of thermal data, and generating an image so as to monitor the physiological portions over time.

25. The method of claim 24, further comprising determining whether the thermal data for a given physiological portion statistically deviates from the thermal data for the remaining physiological portions over time.

26. A system for early detection of a heat-related illness, the system comprising:
a thermal sensor configured to receive thermal signals and generate thermal data from the thermal signals, wherein the thermal sensor has a field of view;
a display; and
a processor coupled with the thermal sensor so as to receive the thermal data from the thermal sensor and coupled with the display, wherein the processor is configured to:
receive, from the thermal sensor, thermal signals from a group that comprises no fewer than three animal subjects that are simultaneously present within the field of view of the thermal sensor while the thermal signals are received;
generate a set of thermal data only from the thermal signals received from the group of simultaneously present animal subjects;
identify, for each animal subject, a subset of the thermal data that corresponds with at least a portion of the animal subject;
determine a baseline for the group of animal subjects from the subsets of thermal data;
compare the subsets of thermal data to the baseline to determine whether the subset of thermal data for any of the animal subjects statistically deviates from the baseline such that the animal subject associated with the statistically deviant thermal data is a thermal outlier relative to the remaining animal subjects; and
communicate with the display such that the display:
generates an image of the field of view of the thermal sensor; and
identifies an animal subject within the image that corresponds to the thermal outlier.

* * * * *